(12) United States Patent
Lee et al.

(10) Patent No.: US 6,451,461 B2
(45) Date of Patent: Sep. 17, 2002

(54) HOLE TRANSPORTING COMPOUNDS HAVING GOOD THERMAL STABILITY FOR ORGANIC ELECTROLUMINESCENT DEVICE AND METHOD FOR PRODUCTION THEREOF

(75) Inventors: Ji-Hoon Lee; In-Seo Kee, both of Taejeon; Sung-Woo Cho, Sungnam-shi; Byung-Hoon Chae, Seoul, all of (KR)

(73) Assignee: Samsung SDI Co., Ltd., Kyungki-do (KR)

( * ) Notice: Subject to any disclaimer, the term of this patent is extended or adjusted under 35 U.S.C. 154(b) by 0 days.

(21) Appl. No.: 09/778,859

(22) Filed: Feb. 8, 2001

(30) Foreign Application Priority Data

Feb. 8, 2000 (KR) .............................................. 00-5814

(51) Int. Cl.$^7$ ...................... H05B 33/12; C07D 487/00
(52) U.S. Cl. ...................... 428/690; 428/704; 428/917; 313/506; 548/440
(58) Field of Search ................. 428/690, 917, 428/704; 313/504, 506; 548/427, 440; 564/412, 433, 434

(56) References Cited

U.S. PATENT DOCUMENTS 3,615,416 A * 10/1971 Fox .............................. 96/1.6

FOREIGN PATENT DOCUMENTS

JP          08-003547 A   *  1/1996  ........... C09K/11/06

* cited by examiner

*Primary Examiner*—Cynthia H. Kelly
*Assistant Examiner*—Dawn Garrett
(74) *Attorney, Agent, or Firm*—Lee & Sterba, P.C.

(57) ABSTRACT

A hole transporting compound for organic electroluminescent devices with good thermal stability, which includes 6,6'-bis(9H,9-carbazolyl)-N,N'-disubstituted-3,3'-bicarbazyl as a basic molecular structure, is represented by the following formula I:

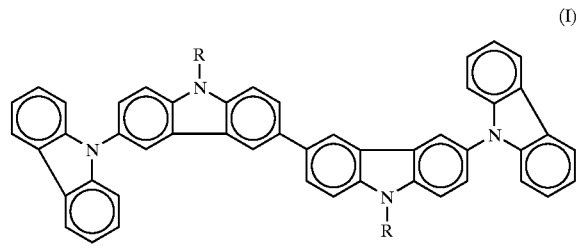

wherein R is a hydrogen atom, a $C_{1-12}$ aliphatic alkyl group, a $C_{3-12}$ branched alkyl group, a $C_{5-12}$ cyclic alkyl group, or a $C_{4-14}$ aromatic group, wherein the aromatic group can have one or more alkoxy or amine substituents,

12 Claims, 9 Drawing Sheets

HOLE TRANSPORTING COMPOUNDS HAVING GOOD THERMAL STABILITY FOR ORGANIC ELECTROLUMINESCENT DEVICE AND METHOD FOR PRODUCTION THEREOF

BACKGROUND OF THE INVENTION

1. Field of the Invention

The present invention relates to a hole transporting compound for organic electroluminescent devices, and to a method for producing the same. More particularly, the present invention relates to a hole transporting compound with a good thermal stability having 6,6'-bis(9H,9-carbazolyl)-N,N'-disubstituted-3,3'-bicarbazyl as a basic molecular structure, and to a method for its production.

2. Description of Background Art

Electronic technology has improved human life since silicon was first used as a semiconductor material. The fast growth of photocommunications and multimedia in particular has accelerated the formation of a highly information-oriented society. Consequently, optoelectronic devices (OEDs) based on the conversion of photons into electrons or vice versa are very important elements in the electronic information industry nowadays. Semiconductive optoelectronic devices can be classified as electroluminescent devices, light-receiving type devices and combined devices.

Most display means are of the light-receiving type, whereas an electroluminescent display (ELD) is a self-luminescent type device. Since the ELD has the advantages of fast responsiveness, obviation of backlight, excellent luminance, as well as wide viewing angle, ELDs have been studied for many applications including natural color display devices. These electroluminescent devices have been developed and practically used in inorganic semiconductors which employ GaN, ZnS and SiC as display devices.

However, an EL device prepared from an inorganic material needs more than 220V for the driving voltage. Furthermore since the preparation of the EL device is carried out by means of a vacuum deposition, a large size device cannot be prepared and the cost of preparation is very high. Thus, not only EL devices using inorganic materials, but also EL devices using organic materials have been developed. Pope et al. disclosed electroluminescence of organic materials in 1963. In 1987, Tang et al. of the Eastmann Kodak company presented a green-emitting device, namely a multi-layer electroluminescent device with 1000 cd/m$^2$ of luminance, and 1% of quantum efficiency at less than 10V, which was prepared by using a pigment with a Π-conjugated structure, called "tris(8-hydroxyquinoline) aluminum: $Alq_3$". Thereafter, research on EL devices using organic materials has been actively pursued.

In particular, low-molecular-weight organic materials for ELDs have advantages such as simple synthetic methods and flexibility of molecular structure via appropriate molecular design. Displays using low-molecular-weight organic materials have been developed in sizes up to 10 inches for fall color displays of the passive matrix type and 3 inches for full color displays of the active matrix type using thin film transistors.

However, the major problems with OEDs are light-emitting efficiency and lifetime. Improved lifetimes of 20,000 hours in blue (Indemitsu), 50,000 hours in green (Eastman Kodak), and 20,000 hours in red (Eastman Kodak) respectively, have been achieved, but the light-emitting efficiency of red and blue requires further improvement. Therefore, there are still some problems remaining before applications in fall color display are beneficial.

Furthermore, it is impossible to achieve a high efficiency and luminance without using a multilayer system which consists of a buffer layer, a hole transporting layer, an electron transporting layer and a hole blocking layer for light-emitting efficiency. In order to achieve high efficiency and luminance in a device, it is necessary for each functional layer to have thermal or electrical stability. In particular, the hole transporting layer material requires thermal and electrical stability because the stability critically affects the lifetime of the device. That is, the molecules with low thermal stability are believed to have low morphological stability, which brings about morphological changes in the organic layers used in the device when voltage is applied. Furthermore, the change may initiate partial crystallization to decrease the light-emitting efficiency, resulting in a reduction in the lifetime of the device.

The glass transition temperature of the TPD [N,N'-bis(3-methylphenyl)-N,N'-diphenyl-(1,1'-biphenyl)-4,4'-diamine] or NPB [N,N'-bis(naphthalene-1-yl)-N,N'-diphenylbenzidine, NPD] frequently used these days are 60° C. and 96° C. respectively, which are not high temperatures. The vacuum deposition layer of the hole transporting layer, which forms a uniform amorphous film, becomes crystallized or aggregated due to the loss of film uniformity, which results in a reduction in the lifetime of the device. It is necessary for the hole transporting layer to have a Tg of more than 100° C. and an operating or storage temperature of 85° C. in order to use the device outdoors or in vehicles. Thus it is important to further improve the thermal stability and high glass transition temperature of hole transporting materials.

Accordingly, the present inventors have developed a hole transporting compound with good thermal stability and high glass transition temperature having 6,6'-bis(9H,9-carbazolyl)-N,N'-disubstituted-3,3'-bicarbazyl as a basic molecular structure, and methods for producing the same, in order to overcome these problems.

SUMMARY OF THE INVENTION

A feature of the present invention is the provision of a hole transporting compound for organic electroluminescent devices with high thermal stability, and a method for producing the same Another feature of the present invention is the provision of a hole transporting compound for organic electroluminescent devices with a high glass transition temperature, and methods for producing the same.

A further feature of the present invention is the provision of a hole transporting compound for organic electroluminescent devices having good electrical stability, and methods for producing the same.

A further feature of the present invention is the provision of an organic electroluminescent device with high luminescence efficiency.

A further feature of the present invention is the provision of an organic electroluminescent device having an extended lifetime.

In accordance with one aspect of the present invention, there is provided a hole transporting compound having the following formula (I) including 6,6'-bis(9H,9-carbazolyl)-N,N'-disubstituted-3,3'-bicarbazyl as a basic molecular structure:

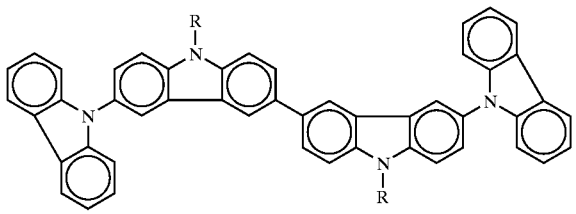

(I)

wherein R is a hydrogen atom, a $C_{1-12}$ aliphatic alkyl group, a $C_{3-12}$ branched alkyl group, a $C_{5-12}$ cyclic alkyl group, or a $C_{4-14}$ aromatic group, more particularly a $C_{6-14}$ aromatic group, wherein the aromatic group can have one or more alkoxy or amine substituents.

DETAILED DESCRIPTION OF THE INVENTION

Figure 1:
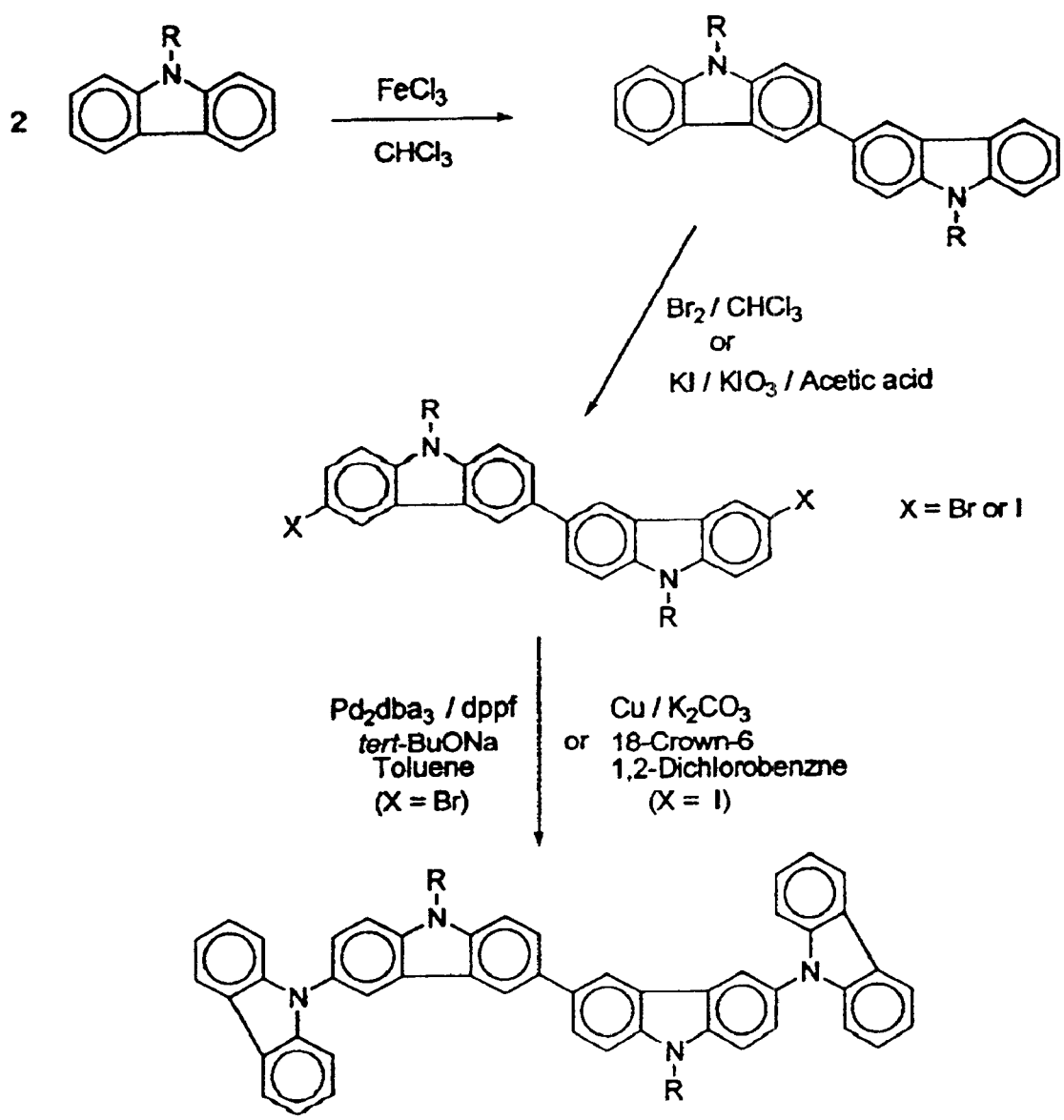
FIG. 1 is a synthetic scheme of preparing a hole transporting compound according to the present invention.
Figure 2:
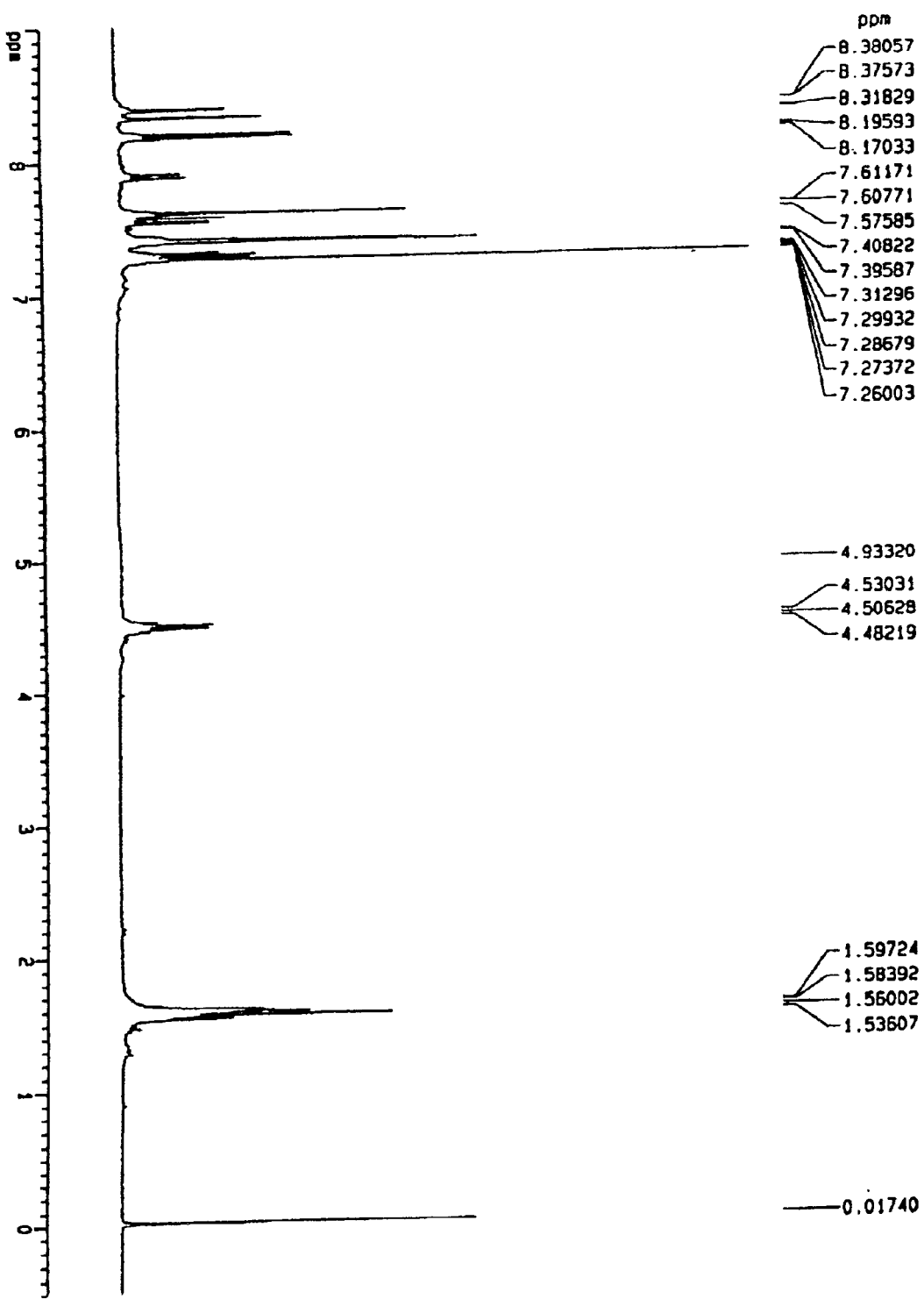
FIG. 2 is a $^1$H-NMR spectrum of BCDC [6,6'-bis(9H,9-carbazolyl)-N,N'-disubstituted-3,3'-bicarbazyl] in accordance with the present invention.
Figure 3:
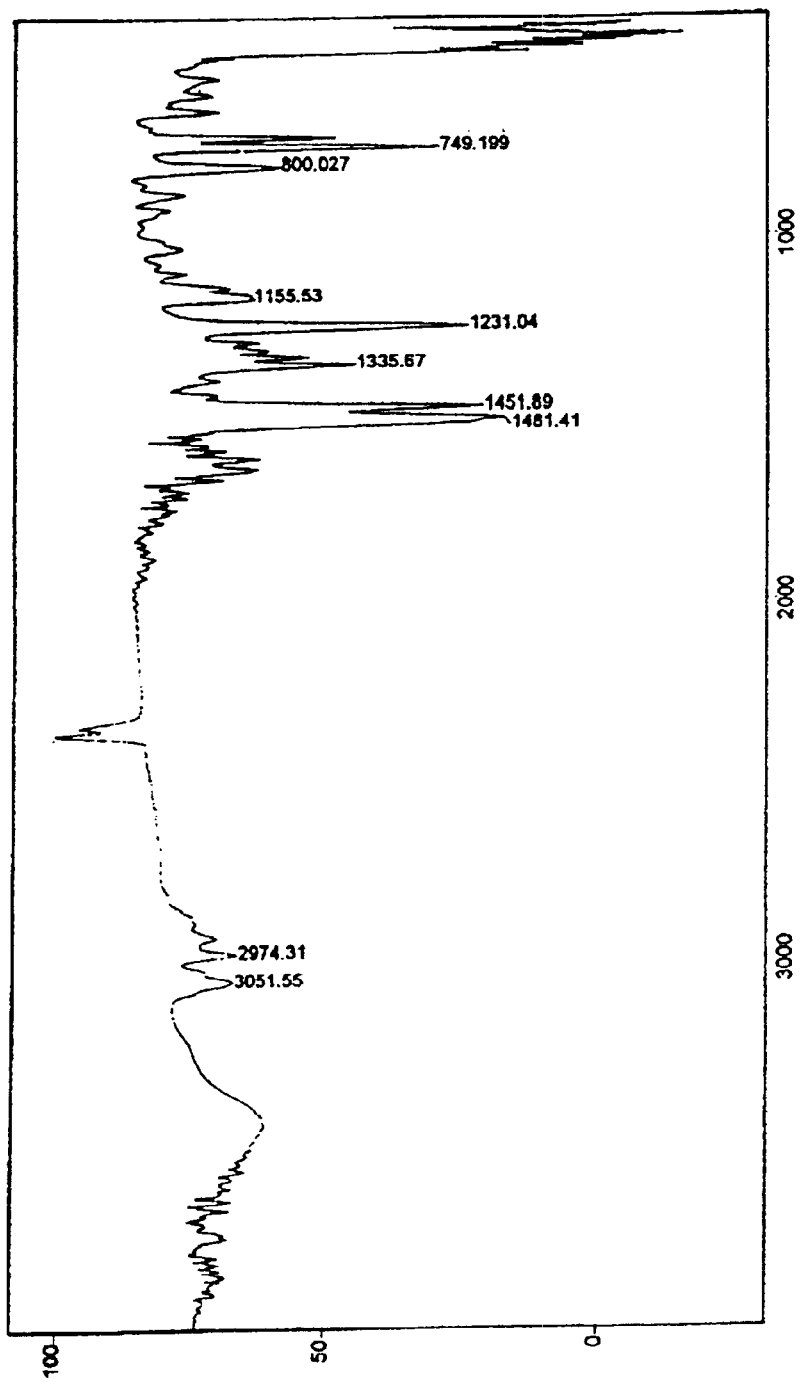
FIG. 3 is a FT-IR spectrum of BCDC in accordance with the present invention.

In organic electroluminescent devices, the driving voltage depends on the facility of hole injection, whereas the light-emission efficiency depends on the efficiency of electron injection. Holes can be more readily injected into light-emission layer than electrons and transport about 20 times as fast as electrons. Accordingly, the major charge carrier in the devices generally are holes.

In general, the emission mechanism in an organic electroluminescent device is as follows. Holes are injected from an anode, and electrons from a cathode. The injected holes and electrons recombine with each other in the emission layer to create singlet exitons. These singlet exitons decay radiatively to release light corresponding to the band-gap energy. At this time, the light-emission efficiency is determined. That is, when the amount of injected holes and electrons are balanced with each other, the light-emission efficiency is at a maximum.

Therefore, it is necessary to balance the mobility and density of holes and electrons to have the same transportation of the carriers. However, holes transport more readily than electrons, which results in an imbalance between the carriers and a consequent decrease in efficiency. Accordingly, a multilayer device with an electron transport layer which has good electron mobility is required to compensate for these shortcomings.

A hole transporting compound of the present invention for organic electroluminescent devices with good thermal stability includes 6,6'-bis(9H,9-carbazolyl)-N,N'-disubstituted-3,3'-bicarbazyl as a basic molecular structure. The hole transporting compound of the present invention is represented by the following formula (I):

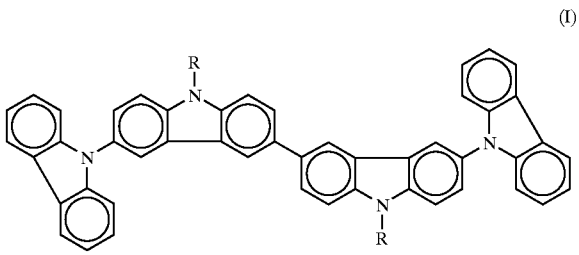

(I)

wherein R is a hydrogen atom, a $C_{1-12}$ aliphatic alkyl group, a $C_{3-12}$ branched alkyl group, a $C_{5-12}$ cyclic alkyl group, or a $C_{4-14}$ aromatic group, more particularly a $C_{6-14}$ group, wherein the aromatic group can have one or more alkoxy or amine substituents.

The disubstituted carbazolyl group of the 6,6' site in the dicarbazyl structure provide a hole transporting compound with not only good thermal stability but also good morphological stability. The twisted aromatic ring induces steric hindrance, resulting in an amorphous bulk structure. The hole transporting compound of the present invention increases the lifetime of the device due to its high thermal stability Methods of preparing the hole transporting compounds of the present invention include the following steps:

(a) Preparing N,N'-disubstituted-3,3'-bicarbazyl represented by the following formula (I)

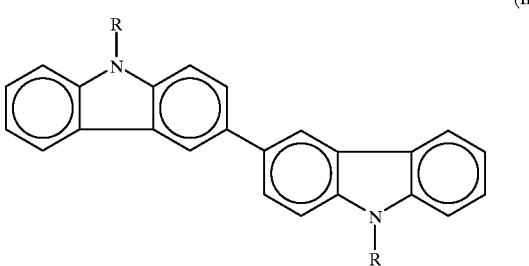

(II)

by dissolving an N-substituted carbazole with chloroform, followed by addition of an iron chloride/chloroform suspension;

(b) Preparing N,N'-disubstituted-6,6'-dihalo-3,3'-bicarbazyl represented by following formula (III)

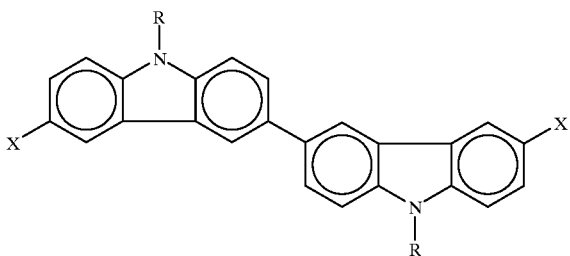

(III)

a by reacting the compound (II) prepared in step (a) with a halogen compound; and (c) Preparing 6,6'-bis(9H,9-carbazolyl)-N,N'-disubstituted-3,3'-bicarbazyl represented by the formula (I) by dissolving compound (III) prepared in step (b) with a solution of an aromatic solvent.

In particular embodiments, R is an ethyl, phenyl, methylphenyl or naphthyl group. Also in particular embodiments when R is an aromatic group, more particular alkoxy substituents include $C_{1-6}$, alkoxy groups, particular amine groups include mono- and dialkyl amines having 1-6 carbon atoms in the alkyl groups. Preferably X is a halogen atom.

In more specific embodiments of the present invention, the halogen compounds added in the second step are $Br_2$, or KI and $KIO_3$, wherein the halogen compounds are dissolved in chloroform and acetic acid respectively.

In additional more specific embodiment of the present invention, the aromatic solvent used in third step (c) is selected depending on the halogen compound added in the second step (b). For example, when $Br_2$ is added at the second step, $Pd_2dba_3$[tris(dibenzylidineacetone) dipalladium], dppf [diphenyl phosphinoferrocene] and tert-BuONa etc. dissolved in toluene can be used in the third step. If KI and $KIO_3$ are added, then Cu, $K_2CO_3$ and 18-Crown-6 in 1,2-dichlorobenzene are beneficially used.

The methods for preparing the hole transporting compounds of the present invention provide the same final target product regardless of the halogen compound added in the second step. That is, as shown in FIG. 1, when $Br_2$ is added in the second step, N,N'-disubstituted-6,6'-dibromo-3,3'-bicarbazyl is prepared, followed by the final product of 6,6'-bis(9H,9-carbazolyl)-N,N'-disubstituted-3,3'-bicarbazyl, which results following dissolution in toluene. If KI and $KIO_3$ are used in the second step, N,N'-disubstituted-6,6'-diiodo-3,3'-bicarbazyl is prepared followed by the same final product, here formed by dissolution in 1,2-dichlorobenzene.

In particular embodiments, organic electroluminescent devices of the present invention have structures selected from the group consisting of: anode/hole transporting layer/emitting layer/cathode; anode/buffer layer/hole transporting layer/emitting layer/cathode; anode/hole transporting layer/emitting layer/electron transporting layer/cathode; anode/buffer layer/hole transporting layer/emitting layer/electron transporting layer/cathode; anode/hole transporting layer/emitting layer/electron transporting layer/hole blocking layer/cathode; or anode/buffer layer/hole transporting layer/emitting layer/electron transporting layer/ hole blocking layer/cathode.

The buffer layer, in particular embodiments, is selected from the group consisting of CuPc (copper phthalocyanine), m-MTDATA [4,4',4"-tris(3-methylphenylphenylamino) triphenylamine], polythiophene, polyaniline, polyacetylene, polypyrrole or polyphenylene vinylene(PPV) derivatives. In particular embodiments, it is preferable to employ LiF or $MgF_2$ as a hole blocking layer. The anode is coated, in specific embodiments, with indium oxide, zinc oxide or the mixture thereof on a flexible substrate such as a glass substrate, PET, polycarbonate or polyimide.

The present invention will be described in more detail by the following Examples. The Examples are given only to illustrate the present invention and are not intended in any way to limit the scope of the invention.

EXAMPLES

Example 1

Preparation of 6,6'-bis (9H,9-carbazolyl)-N,N'-diethyl-3,3'-bicarbazyl] (BCDC)

(1) Synthesis of N,N'-diethyl-3,3'-bicarbazyl 20 g (99.35 mmol) of N-ethylcarbazole is added to a 250 mL Schlenk flask and dissolved by 150 mL of chloroform. To this solution is dropped 64.46 g (0.397 mol) of 4.0 eq $FeCl_3$ after being suspended in 100 mL of chloroform. The solution slowly become dark green due to the formation of carbazole cation radicals. After 24 hours, the reaction mixture was poured into a large amount of MeOH, and the resulting precipitate was filtered. Thereafter, the resulting precipitate was washed three times with a large amount of MeOH and water. The product was dried to give a 95% yield. The dried product can be further purified by silica gel chromatography using 3:1 ethyl acetate/n-hexane as an eluent. The structure was confirmed by $^1$H-NMR: $^1$H-NMR ($CDCl_3$): δ1.50 (t, 6H, 2-$CH_3$), 4.45 (quartet, 4H, 2-$NCH_2$), 7.26B 8.5 (m, 14H, aromatic protons)

(2) Synthesis of N,N'-diethyl-6,6'-dihalo-3,3'-bicarbazyl

A. Preparation of N,N'-diethyl-6,6'-dibromo-3,3'-bicarbazyl 4 g (10 mmol) of N,N'-diethyl-3,3'-bicarbazyl is added to a 100 mL Schlenk flask and dissolved by 50 mL of chloroform. To this solution is dropped 5.0 g (31 mmol) of 3.0 eq bromine after being dissolved by 10 mL of chloroform. The temperature was maintained at 0° C. by using an ice bath. The solution slowly became dark green. After 30-40 minutes, the reaction mixture was poured into a large amount of water, and then was washed with 1.0 N NaOH (aq) several times. The separated chloroform layer was poured into MeOH and the resulting precipitate was filtered. Thereafter the resulting precipitate was washed with a large amount of MeOH and water many times. The product was dried to give a 90% yield. The dried product can be further purified by silica gel chromatography using 3:1 ethyl acetate/n-hexane as an eluent. The structure was confirmed by $^1$H-NMR: : $^1$H-NMR ($CDCl_3$): δ1.46 (t, 6H, 2-$CH_3$), 4.34 (quartet, 4H, $2NCH_2$), 7.26B 8.33 (m, 12H, aromatic protons)

B. Preparation of N,N'-diethyl-6,6'-diiodo-3,3'-bicarbazyl 3 g (7.72 mmol) of N,N'-diethyl-3,3'-bicarbazyl, 3.46 g (20.85 mmol) of KI and 96 g (23.2 mmol) of $KIO_3$ were added to a 100 mL Schlenk flask, followed by charging the flask with 70 to 80 mL of acetic acid. The solution was heated to 70° C. After 20-30 minutes, the reaction mixture was poured into a large amount of water, followed by washing with 1.0 N NaOH (aq) several times, and then extracted by using chloroform. The separated chloroform layer was poured into MeOH and the resulting precipitate was filtered. Thereafter, the resulting precipitate was washed with a large amount of MeOH and water many times. The product was dried to give an 88% yield. The dried product can be further purified by silica gel chromatography using 4:1 ethyl acetate/n-hexane as an eluent. The structure was confirmed by $^1$H-NMR: $^1$H-NMR (CDCl$_3$): δ1.50 (t, 6H, 2-CH$_3$), 4.38 (quartet, 4H, 2-NCH$_2$), 7.21B 8.5 (m, 12H, aromatic protons)

(3) Synthesis of 6,6'-bis(9H, 9-carbazolyl)-N,N'-diethyl-3,3'-bicarbazyl] (BCDC)

A. 0.0755 g (8.25×10$^{-5}$ mol) of tris(dibenzylidineacetone)dipalladium (Pd$_2$dba$_3$), 0.0686 g (1.238×10$^{-5}$ mol) of diphenyl phosphinoferrocene (dppf), and 1.5 g (2.75 mmol) of N,N'-diethyl-6,6'-dibromo-3,3'-bicarbazyl were dissolved by 40-50 mL of anhydrous toluene, followed by stirring for 20 minutes. To the reaction mixture was added 0.92 g of carbazole (5.50 mmol, recrystallized from EtOH) and 0.817 g (8.25 mmol) of sodium tert-butoxide in another flask. The final reaction mixture was agitated for 15 minutes and then heated to reflux for 18 hours. The reaction was monitored by TLC. When the carbazole disappeared, the temperature was reduced to room temperature, and then 10 mL of 1.0 M HCl (aq) was added into the reaction mixture. After agitating for 5 minutes, the reaction mixture was poured into a large amount of MeOH and the resulting precipitate was filtered. The product was dried to give a 90% yield. The dried product was purified by silica gel chromatography. The structure was confirmed by $^1$H-NMR: $^1$H-NMR (CDCl$_3$): δ1.56 (t, 6H, 2-CH$_3$), 4.51 (quartet, 4H, 2-NCH$_2$—), 7.27B 8.39 (m, 28H, aromatic protons).

B. 2 g (3.12 mmol) of N,N'-diethyl-6,6'-diiodo-3,3'-bicarbazyl, 1.045 g (6.25 mmol, recrystallized from EtOH) of carbazole, 0.4 g (6.25 mmol) of activated Cu, 1.76 g (12.48 mmol) of potassium carbonate, and 0.25 g (3 mol%) of 18-crown-6 were dissolved by 30-40 mL of 1,2-dichlorobenzene, followed by reaction for 2-3 days at 180° C. All reagents were transferred under an N$_2$ atmosphere. The reaction was monitored by TLC. When the carbazole disappeared, the temperature was lowered, and the reaction mixture was then poured into a large amount of MeOH. The resulting precipitate was filtered, and the product was dried to give a 95% yield. The dried product was purified by silica gel chromatography. The structure was confirmed by $^1$H-NMR: $^1$H-NMR (CDCl$_3$): δ1.56 (t, 6H, 2-CH$_3$), 4.51 (quartet, 4H, 10 2-NCH$_2$—), 7.27B 8.39 (m, 28H, aromatic protons)

Example 2

Preparation of 6,6'-bis(9H1,9-carbazolyl)-N,N'-diphenyl-3,3'-bicarbazyl (1) Synthesis of N,N'-diethyl-3,3'-bicarbazyl 4.85 g (19.93 mmol) of N-phenylcarbazole was added to a 250 mL Schienk flask and dissolved by 75 mL of chloroform. To this solution was dropped 12.93 g (79.7 mmol) of 4.0 eq FeCl$_3$ suspended by 80 mL of chloroform. The solution slowly become dark green due to the formation of carbazole cation radicals. After 24 hours, the reaction mixture was poured into a large amount of MeOH and the resulting precipitate was filtered. Thereafter the resulting precipitate was washed three times with a large amount of MeOH and water and then dissolved by hot chloroform. After removing the insoluble precipitate, the solution was poured into MeOH again. The product was dried to give a 93% yield. The dried product can be further purified by silica gel chromatography using 4:1 ethyl acetate/n-hexane as an eluent. The structure was confirmed by $^1$H-NMR: $^1$H-NMR (CDCl$_3$): δ7.34B 8.48 (m, 24H, aromatic protons).

(2) Synthesis of N,N'-diphenyl-6,6'-dihalo-3,3'-bicarbazyl
A. Preparation of N,N'-diphenyl-6,6'-dibromo-3,3'-bicarbazyl 4.87 g (10 mmol) of N,N'-diphenyl-3,3'-bicarbazyl was added to a 100 mL Schlenk flask and dissolved by 50 mL of chloroform. To this solution was dropped 5.0 g (31 mmol) of 3.0 eq bromine dissolved by 10 mL of chloroform. The temperature was maintained at 0° C. using an ice bath. The solution slowly became dark green. After 40-50 minutes, the reaction mixture was poured into a large amount of water followed by washing with 1.0 N NaOH (aq) several times. The separated chloroform layer was poured into MeOH and the resulting precipitate was filtered. Thereafter the resulting precipitate was washed with a large amount of MeOH and water many times. The product was dried to give an 85% yield. The dried product can be further purified by silica gel chromatography using 3:1 ethyl acetate/n-hexane as an eluent. The structure was confirmed by $^1$H-NMR: $^1$H-NMR (CDCl$_3$): δ7.25B 8.38 (m, 22H, aromatic protons).

B. Preparation of N,N'-diphenyl-6,6'-diiodo-3,3'-bicarbazyl 3.76 g (7.72 mmol) of N,N'-diphenyl-3,3'-bicarbazyl, 3.46 g (20.85 mmol) of KI, 4.96 g (23.2 mmol) of KIO$_3$ is added to a 100 mL Schlenk flask followed by charging the flask with 70 to 80 mL of acetic acid. The solution was heated to 70° C. After 20-30 minutes, the reaction mixture was poured into a large amount of water followed by washing with 1.0 N NaOH (aq) several times and then extracted by chloroform. The separated chloroform layer was poured into MeOH and the resulting precipitate was filtered. Thereafter, the resulting precipitate was washed with a large amount of MeOH and water many times. The product was dried to give an 85% yield. The dried product can be further purified by silica gel chromatography using 4:1 ethyl acetate/n-hexane as an eluent. The structure was confirmed by $^1$H-NMR: $^1$H-NMR (CDCl$_3$): δ7.23B 8.5 (m, 22H, aromatic protons)

(3) Synthesis of 6,6'-bis(9H,9-carbazolyl)-N,N'-diphenyl-3,3'-bicarbazyl

A. 0.0855 g (9.34×10$^{-5}$ mol) of tris(dibenzylidineacetone)dipalladium (Pd$_2$dba$_3$), 0.0776 g (1.40×10$^{-4}$ mol) of diphenyl phosphinoferrocene (dppf) and 2.0 g (3.11 mmol) of N,N'-diphenyl-6,6'-dibromo-3,3'-bicarbazyl were dissolved by about 50 mL of anhydrous toluene, followed by stirring for 20 minutes. To the reaction mixture were added 1.04 g (6.22 mmol, recrystallized from EtOH) of carbazole and 0.898 g (9.34 mmol) of sodium tert-butoxide in another flask. The final reaction mixture was agitated for 20 minutes and then heated to reflux for 24 hours. The reaction was monitored by TLC. When the carbazole disappeared, the temperature was lowered followed by addition of 10 mL of 1.0 M HCl (aq). After agitating for 5 minutes, the reaction mixture was poured into a large amount of MeOH, and the resulting precipitate was filtered. The product was dried to give a 91% yield. The dried product was purified by silica gel chromatography. The structure was confirmed by $^1$H-NMR: $^1$H-NMR (CDCl$_3$): δ7.26B 8.41 (m, 38H, aromatic protons).

B. 2 g (3.12 mmol) of N,N'-diethyl-6,6'-diiodo-3,3'-bicarbazyl, 1.045 g (6.25 mmol, recrystallized from EtOH) of carbazole, 0.4 g (6.25 mmol) of activated Cu, 1.76 g (12.48 mmol) of potassium carbonate and 0.25 g (3 mol %) of 18-crown-6 were dissolved by 30~40 mL of 1,2-dichlorobenzene, followed by reaction for 2-3 days at 180° C. All agents were transferred under an N$_2$ atmosphere. The reaction was controlled by TLC. When the carbazole disappeared, the temperature was lowered, and the mixture was poured into a large amount of MeOH. The resulting precipitate was filtered, and the product was dried to give a 90% yield. The dried product was purified by silica gel chromatography. The structure was confirmed by $^1$H-NMR: $^1$H-NMR (CDCl$_3$): δ7.26B 8.41 (m, 38H, aromatic protons).

EL Device Fabrication

Figure 8:
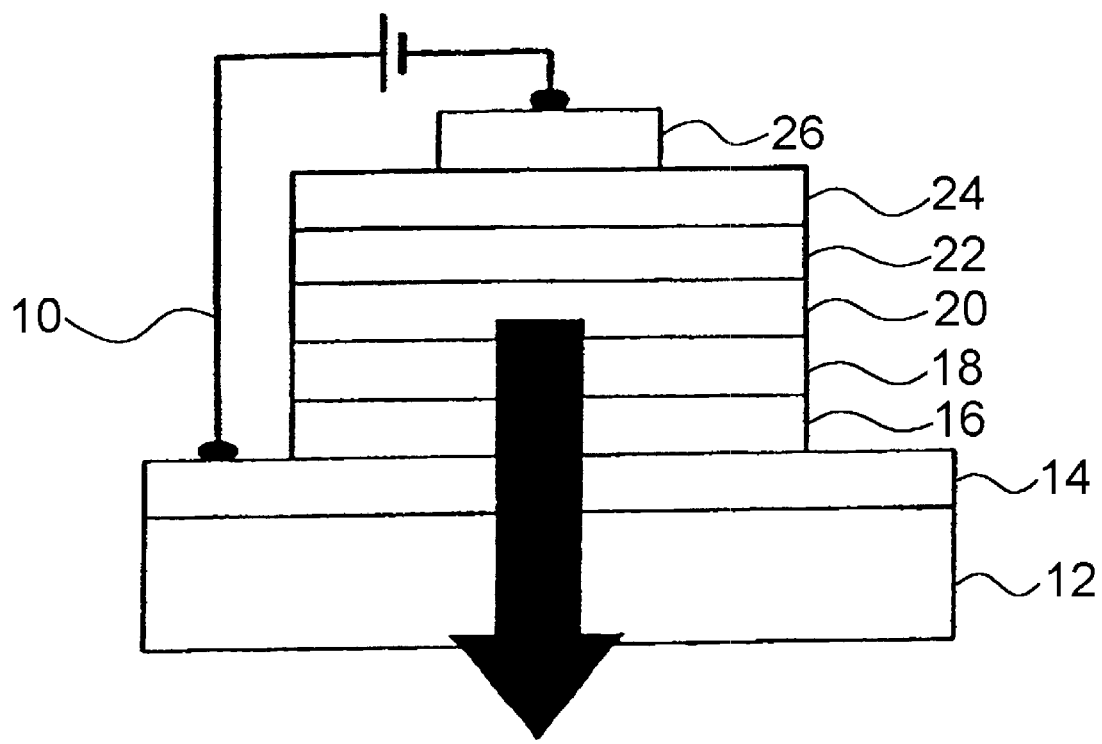
FIG. 8 is a cross-section of an electroluminescent device prepared by a hole transporting compound in accordance with the present invention.

All EL devices were fabricated by using a hole transporting compound prepared according to example 1. The structure of an exemplary fabricated EL device 10 is illustrated in FIG. 8, and included the following elements: a glass substrate 12, an indium-tin-oxide (ITO) layer (anode) 14, a buffer layer 16, a hole transporting layer (HTL) 18, an emitting layer (EML) 20, an electron transporting layer (ETL) 22, a hole blocking layer (HBL) 24, and a cathode 26 formed, for example, of Al, Al:Li, Mg:Ag or Ca.

The electroluminescent devices were constructed in the following manner:

a) An indium-tin-oxide coated glass substrate was cleaned and then patterned with a target form by using a photoresist resin and an etchant b) The substrate was sequentially ultrasonicated in acetone and IPA (isopropyl alcohol) for 20 minutes respectively and treated with boiling IPA, followed by UV-ozone cleaning for 15 minutes.

c) A buffer layer of CuPc (1 Å/sec) was then deposited on top of the ITO coated substrate to a thickness of about 20 um, followed by a hole transporting layer according to the present invention (50 nm, 1 Å/sec), an emitting layer of $Alq_3$ (70 nm, 1 Å/sec) or $Alq_3$ (30 nm) doped with 1.5% of coumarin 6 (0.015 Å/sec) (the latter preferably being further coated with an electron transporting layer of $Alq_3$ (40 nm)), an electron transporting layer and hole blocking layer of LiF (1 nm, 0.1 Å/sec) and a cathode of Al (200 nm, 10 Å/sec), and then encapsulated with metal under a dry $N_2$ atmosphere.

d) The pressure was maintained less than $1 \times 10^{-6}$ torr. The layer thicknesses and the film growth rate of vapor deposition were controlled by using a crystal sensor. The luminescent area was 4 mm$^2$. The direct current of forward bias voltage was used for the driving voltage.

The voltage and the luminance were determined by scanning at 10B 100 mA/cm$^2$ in constant current using Keithley SMU238 and BM7. The device with a structure of ITO/CuPc (20 nm)/BCDC (50 nm)/$Alq_3$ (70 nm)/LiF (1 nm)/Al (200 nm) had a luminance of 3500 cd/m$^2$ at a voltage of 11.32 V in 100 mA/cm$^2$. When the device structure was $C_6$-doped ITO/CuPc (20 nm)/BCDC (50 nm)/$Alq_3$+1.5%$C_6$ (30 nm)/$Alq_3$ (40 nm)/LiF (1 nm)/Al (200 nm), the luminance was 10,290 cd/m$^2$ at a voltage of 12.47 V in 100 mA/cm$^2$.

Physical Property Measurement (1) Optical Property

Figure 4:
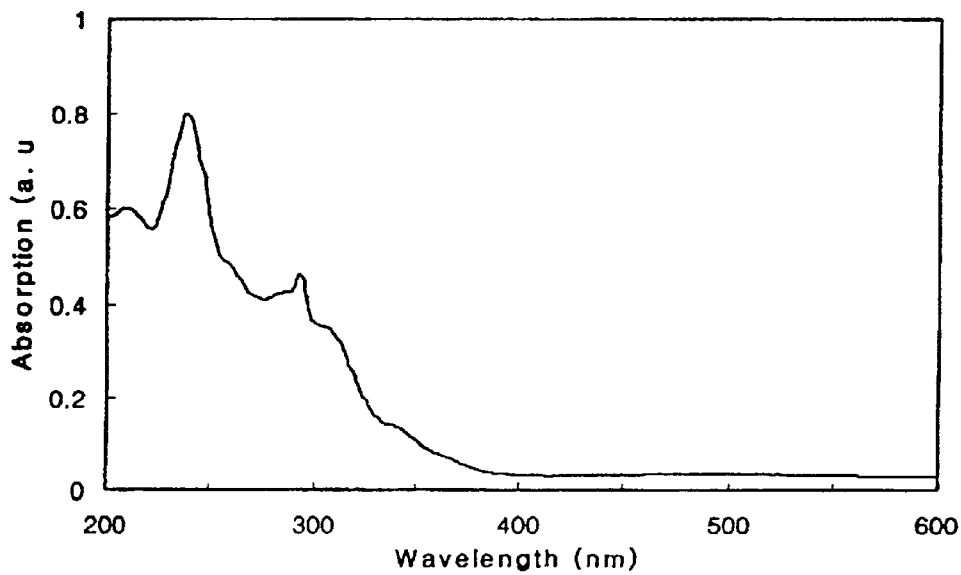
FIG. 4 is an UV-Visible spectrum of BCDC in accordance with the present invention.
Figure 5:
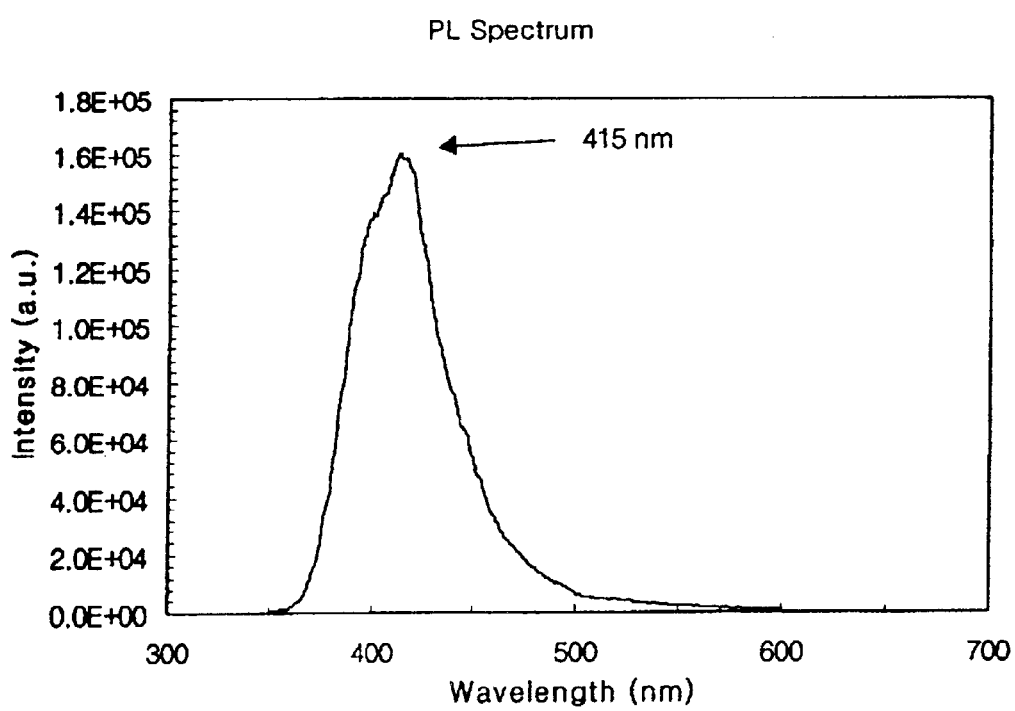
FIG. 5 is a photoluminescence spectrum of BCDC in accordance with the present invention.

The hole transporting compound formed in Example 1 was mixed with PMMA in the ratio of 1:10 (weight %), and then spin-coated on quartz to form a polymer thin-film layer, followed by measurement of UV absorption peaks and the photoluminescence spectrum (PL spectrum). The results are shown in FIGS. 4 and 5, respectively. The UV absorption peaks of BCDC were 238, 293, 306 and 340 nm, and the PL spectrum at 320 nm of excitation wavelength had a maximum PL peak at 415 nm.

(2) Thermal Property

Figure 6:
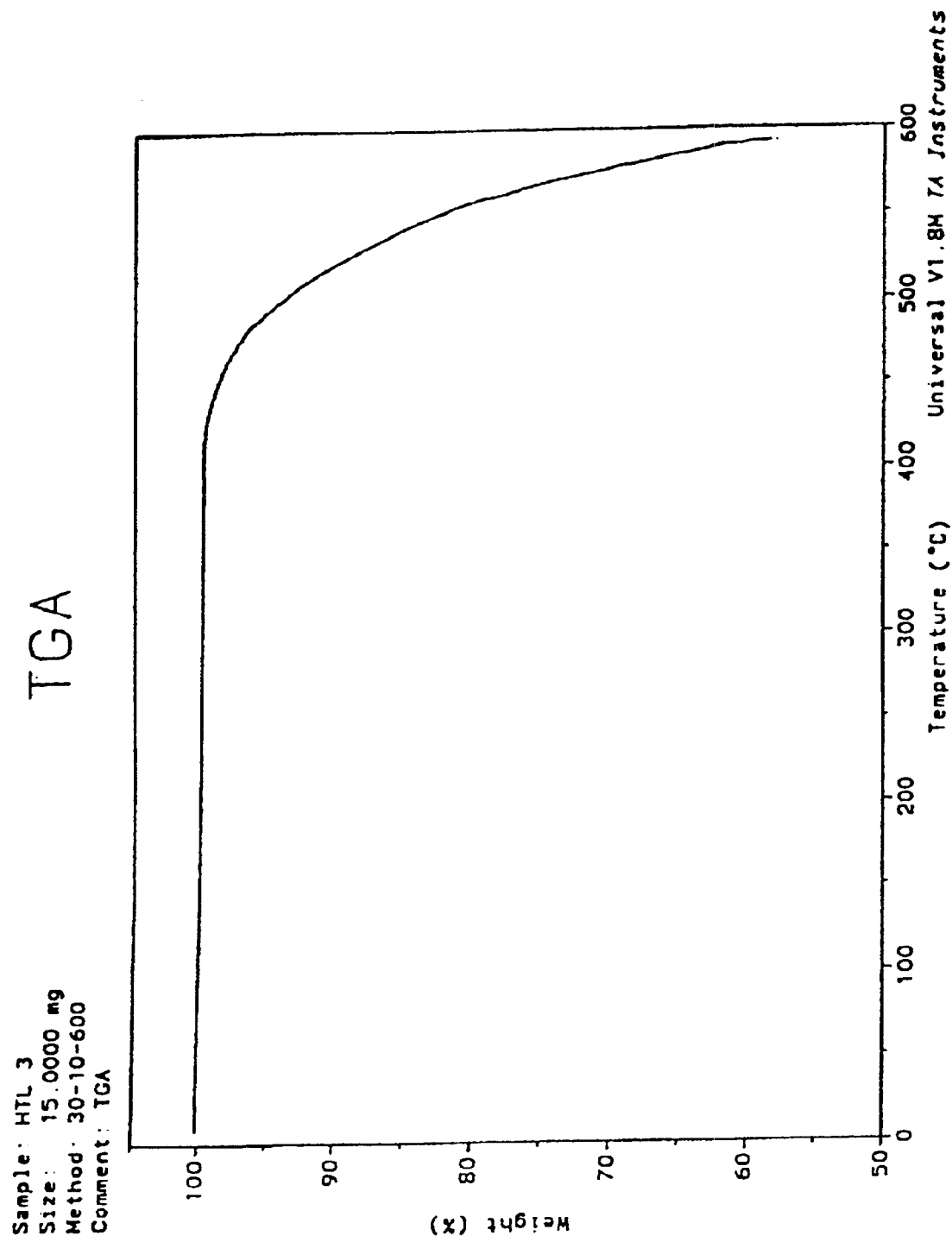
FIG. 6 is a TGA curve of BCDC in accordance with the present invention.
Figure 7:
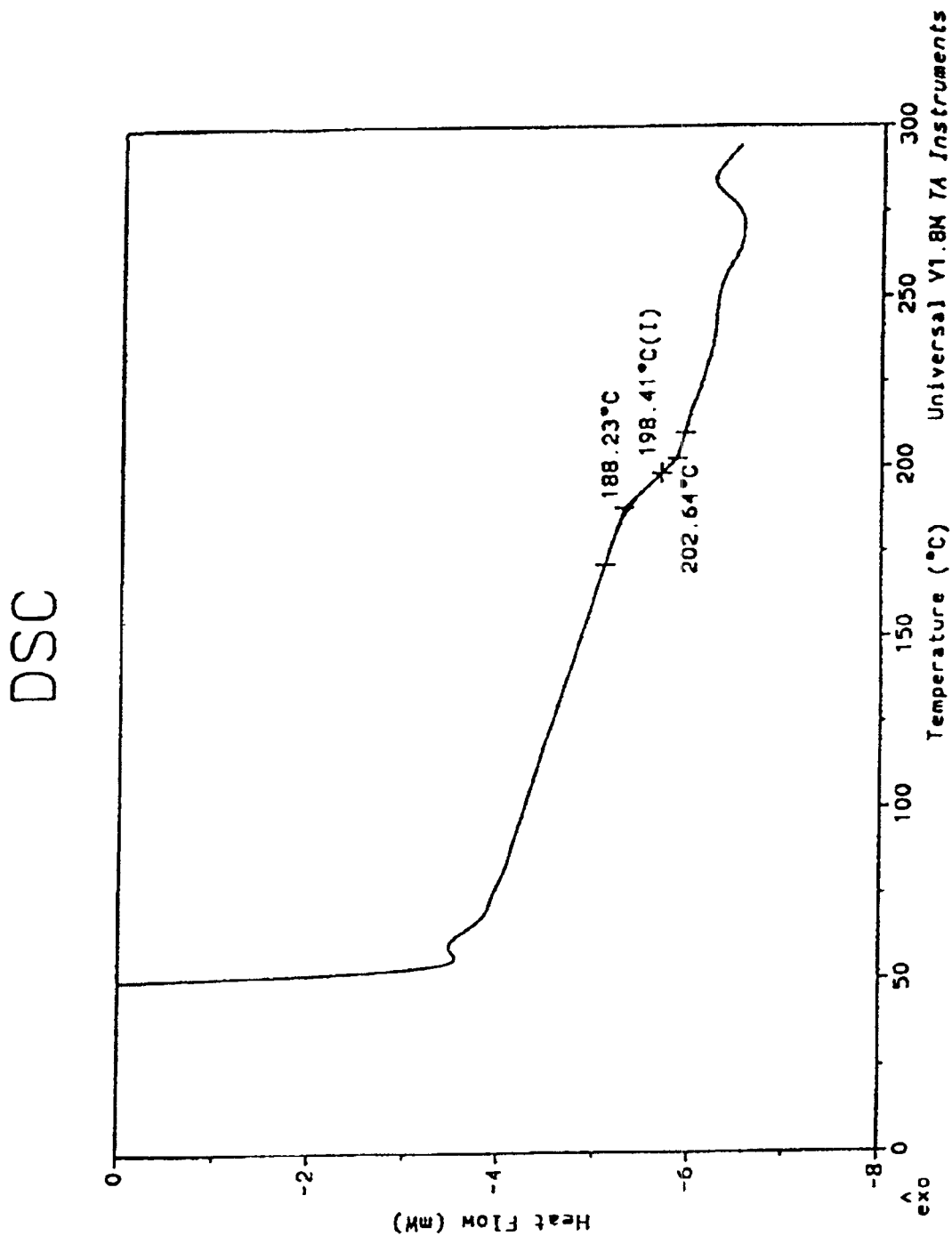
FIG. 7 is a DSC curve of BCDC in accordance with the present invention.

The thermal property of the foregoing hole transporting compound according to the present invention was measured by TGA (thermogravimetric analysis) and DSC(differential scanning calorimetry) at the rate of 10° C./min under an $N_2$ atmosphere. The results are shown in FIGS. 6 and 7. In the case of BCDC, 5% of weight loss was observed near 500° C., about 50 weight % remained near 600° C. The glass transition temperature (Tg) was determined to be about 200° C. by DSC. Accordingly, the glass transition temperature (Tg) of the hole transporting compound of the present invention is much higher than that of TPD [N,N'-bis(3-methyl-phenyl)-N,N'-diphenyl-(1,1'-biphenyl )-4,4'-diamine] or NPB of the prior art (Tg of 60° C. and 96° C. respectively).

(3) Electroluminescent Property

The electroluminescent property of the exemplary EL device of the present invention was measured by comparing ITO/CuPc (20 nm)/BCDC (50 um) /$Alq_3$ (70 nm)/LiF (1 nm)/Al (200 um) as a standard device with ITO/CuPc (20 nm)/NPB (50 nm)/$Alq_3$ (70 nm)/LiF (1 nm)/Al (200 nm) as a comparative device. A coumarin 6 ($C_6$) doped device was used to increase the emitting efficiency and had the following structure: ITO/CuPc (20 nm)/BCDC (50 nm)/$Alq_3$+1.5% $C_6$ (30 nm)/$Alq_3$ (40 nm)/LiF (1 nm)/Al (200 nm), and the comparative device was ITO/CuPc (20 nm)/NPB (50 nm)/$Alq_3$+1.5% $C_6$ (30 nm)/$Alq_3$ (40 nm)/LiF (1 nm)/Al (200 nm).

FIG. 8 is a cross-section of an electroluminescent device prepared using a hole transporting compound in accordance with the present invention. The luminescence arose from $Alq_3$ and coumarin 6. The exciplex between the hole transporting layer 18 and the emitting layer 20 was not observed. All active areas showed an even source of light, and the rectification property was good.

Figure 9:
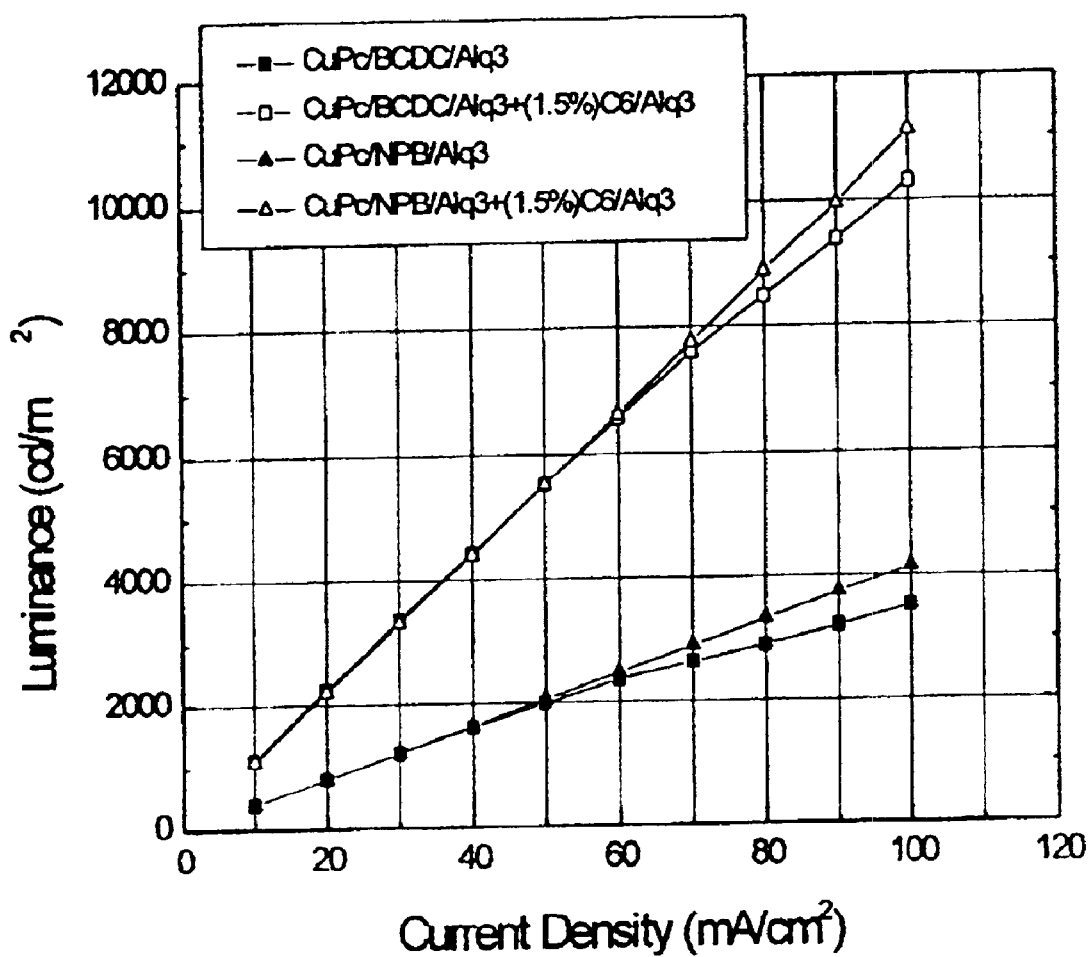
FIG. 9 is a current density-luminance plot for electroluminescent devices of [ITO/CuPc/BCDC/Alq$_3$/LiF/Al] and [ITO/CuPc/BCDC/Alq$_3$+(1.5% coumalin 6/Alq$_3$/LiF/Al) prepared by using BCDC in accordance with the present invention.
Figure 10:
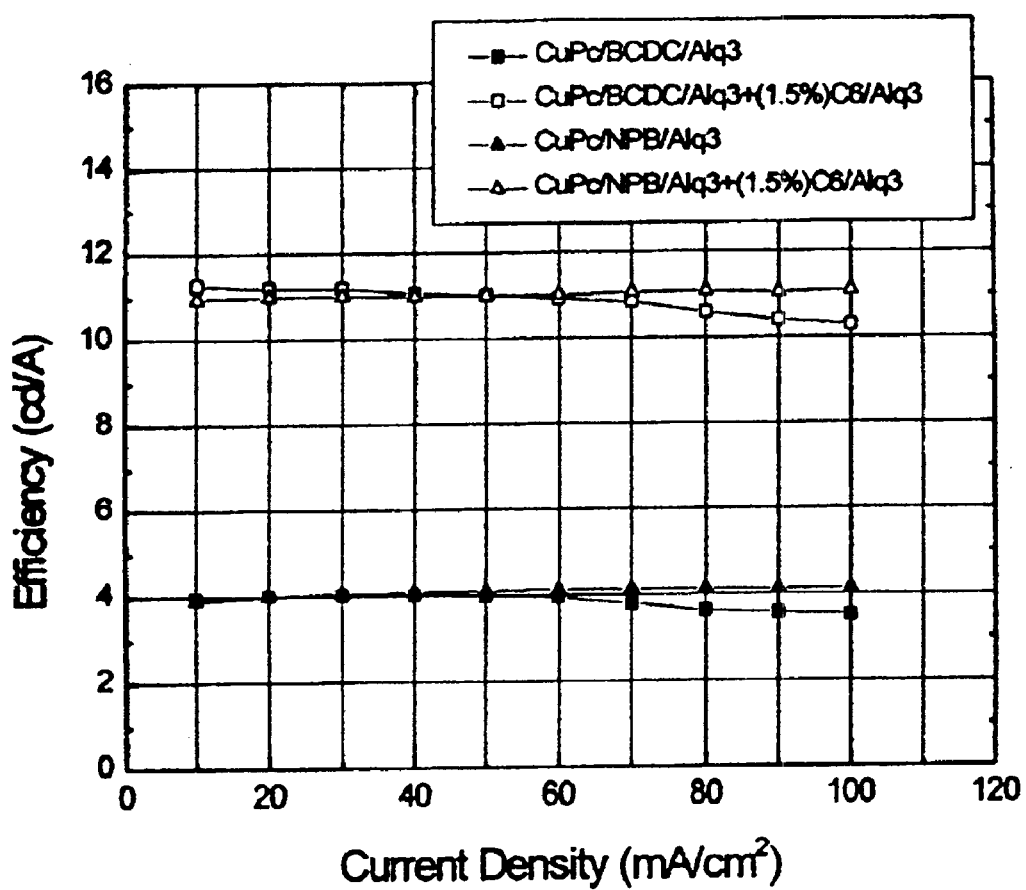
FIG. 10 is a current density-emitting efficiency plot for electroluminescent devices of [ITO/CuPc/BCDC/Alq$_3$/LiF/Al] and [ITO/CuPc/BCDC/Alq$_3$+(1.5% coumalin 6/Alq$_3$/LiF/Al) prepared by using BCDC in accordance with the present invention.

FIG. 9 is a plot including current density-luminance curves for electroluminescent devices prepared in accordance with the present invention. FIG. 10 is a plot including current density-emitting efficiency curves (cd/A).

Comparing L-I efficiency, in the case of low current density, the efficiency of a device using BCDC (4.0 cd/A) as a hole transporting layer was higher than that of a device using NPB (3.9 cd/A). On the other hand, in high current density, the efficiency of the device using BCDC (3.5 cd/A) was lower than that of a device using NPB (4.1 cd/A).

A similar phenomenon was observed in the device systems doped with coumarin 6. That is, in low current density, the L-I efficiency of a device using BCDC (11.3 cd/A) as a hole transporting layer was higher than that of a device using NPB (11.0 cd/A). On the other hand, in high current density, the efficiency of a device using BCDC (10.3 cd/A) was somewhat lower than that of a device using NPB (11.1 cd/A). Meanwhile, a lifetime test showed that the device using BCDC as a hole transporting layer showed better durability and repeatability than the device using NPB, due to the enhanced thermal stability of BCDC used as a hole transporting layer.

What is claimed is:

1. A hole transporting compound for organic electroluminescent devices represented by the following formula I

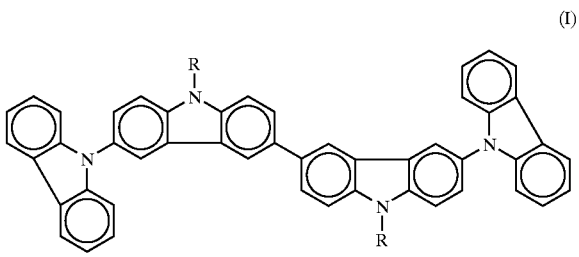

(I)

wherein R is a hydrogen atom, a $C_{1-12}$ aliphatic alkyl group, a $C_{3-12}$ branched alkyl group, a $C_{5-12}$ cyclic alkyl group, or a $C_{4-14}$ aromatic group, wherein the aromatic group can have one or more alkoxy or amine substituents.

2. A hole transporting compound of claim 1, wherein R is a C$_{6-14}$ aromatic group.

3. A hole transportation compound of claim 1, wherein R is an ethyl group.

4. A hole transporting compound of claim 1, wherein R is a phenyl group, a methylphenyl group or a naphthyl group.

5. An organic electroluminescent device comprising a hole transporting layer which comprises a compound in claim 1, the device having a structure selected from the group consisting of:
  anode/hole transporting layer/emitting layer/cathode,
  anode/buffer layer/hole transporting layer/emitting layer/cathode,
  anode/hole transporting layer/emitting layer/electron transporting layer/cathode,
  anode/buffer layer/hole transporting layer/emitting layer/electron transporting layer/cathode,
  anode/hole transporting layer/emitting layer/electron transporting layer/hole blocking layer/cathode, and
  anode/buffer layer/hole transporting layer/emitting layer/electron transporting layer/hole blocking layer/cathode.

6. A organic electroluminescent device of claim 5, wherein said buffer layer is selected from the group consisting of CuPc (copper phthalocyanine), m-MTDATA, polythiophene, polyaniline, polyacetylene, polypyrrole and polyphenylene vinylene(PPV) derivatives.

7. An organic electroluminescent device of claim 5 wherein said hole blocking layer comprises LiF or MgF$_2$.

8. An organic electroluminescent device of claim 5 wherein said anode comprises a substrate and a coating layer.

9. An organic electroluminescent device of claim 8 wherein said coating layer comprises indium oxide, zinc oxide or the mixture thereof.

10. An organic electroluminescent device of claim 8 wherein said flexible substrate comprises glass, PET, polycarbonate or polyimide.

11. A method of preparing a hole transporting compound for organic electroluminescent devices represented by the following formula I

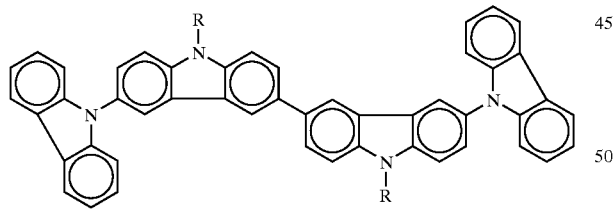

(I)

wherein R is a hydrogen atom, a C$_{1-12}$ aliphatic alkyl group, a C$_{3-12}$ branched alkyl group, a C$_{5-12}$ cyclic alkyl group, or a C$_{4-14}$ aromatic group, wherein the aromatic group can have one or more alkoxy or amine substituents,
which comprises the steps of:
  (b) preparing an N,N'-disubstituted-3,3'-bicarbazyl represented by the following formula (II)

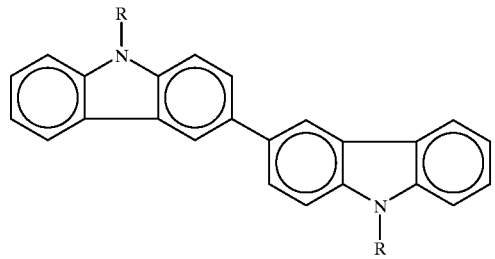

(II)

by dissolving an N,N'-substituted carbazole with chloroform, followed by addition of an iron chloride/chloroform suspension;

(b) preparing N,N'-disubstituted-6,6'-dihalo-3,3'-bicarbazyl represented by following formula (III)

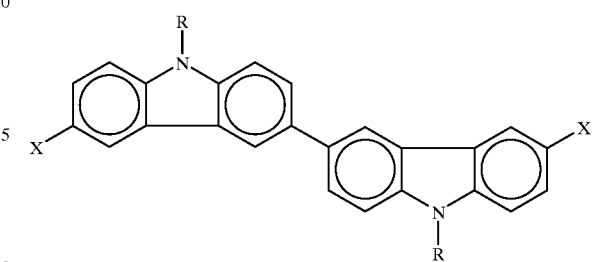

(III)

a by reacting the compound (II) prepared in step (a) with a halogen compound;
and
(c) preparing 6,6'-bis(9H,9-carbazolyl)-N,N'-disubstituted-3,3'-bicarbazyl represented by the formula (I) by dissolving compound (III) prepared in step (b) with a solution of an aromatic solvent.

12. A method of claim 11 wherein in step (b) the halogen compound is selected from the group consisting of Br$_2$ and a mixture of KI and KIO$_3$.

* * * * *